United States Patent
Lee et al.

(10) Patent No.: US 7,429,682 B2
(45) Date of Patent: Sep. 30, 2008

(54) CATALYST FOR PARTIAL OXIDATION OF METHYLBENZENES, METHOD FOR PREPARING THE SAME, AND METHOD FOR PRODUCING AROMATIC ALDEHYDES USING THE SAME

(75) Inventors: Won Ho Lee, Daejeon (KR); Hyun Kyung Yoon, Seoul (KR); Dong Il Lee, Gyeonggi-do (KR); Jong Hyun Chae, Daejeon (KR); Ji Hyang Son, Busan (KR); In Kyu Park, Daejeon (KR); Won Jae Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 11/603,213

(22) Filed: Nov. 22, 2006

(65) Prior Publication Data

US 2008/0021248 A1  Jan. 24, 2008

(30) Foreign Application Priority Data

Jul. 19, 2006 (KR) .................. 10-2006-0067396

(51) Int. Cl.
*C07C 45/00* (2006.01)
*B01J 23/00* (2006.01)
*B01J 21/00* (2006.01)
*B01J 20/00* (2006.01)

(52) U.S. Cl. .............. 568/431; 502/254; 502/306; 502/307; 502/308; 502/309; 502/310; 502/311; 502/312; 502/313; 502/314; 502/315; 502/316; 502/317; 502/318; 502/319; 502/320; 502/323; 502/324; 502/349; 502/350; 502/355; 502/415; 502/439

(58) Field of Classification Search ............... 502/254, 502/305, 317, 306, 307, 308, 309, 310, 311, 502/312, 313, 314, 315, 316, 318, 319, 320, 502/323, 324, 349, 350, 355, 415, 439; 568/431
See application file for complete search history.

(56) References Cited

U.S. PATENT DOCUMENTS 3,845,137 A  10/1974  Magder
4,017,547 A   4/1977  Smmons et al.

(Continued)

FOREIGN PATENT DOCUMENTS

JP  47-002086  1/1972

(Continued)

*Primary Examiner*—Cam N. Nguyen
(74) *Attorney, Agent, or Firm*—McKenna Long & Aldridge LLP

(57) ABSTRACT

A catalyst for gas phase oxidation of methylbenzenes in the presence of molecular oxygen to produce corresponding aromatic aldehydes, a method for preparing the catalyst, and a method for producing aromatic aldehydes from methylbenzenes by using the catalyst. The catalyst comprises a compound represented by the following formula (1):

$$W_a X_b Y_c O_x \qquad (1)$$

wherein W represents a tungsten atom, X represents one or more alkali metals selected from the group consisting of Li, Na, K, Rb, and Cs, Y represents one or more elements selected from the group consisting of Fe, Co, Ni, Cu, Mn, Re, Cr, V, Nb, Ti, Zr, Zn, Cd, Y, La, Ce, B, Al, Sn, Mg, Ca, Sr, and Ba, O stands for an oxygen atom, and the ratio of a:b:c is 12:0.001~1:0~5.

13 Claims, 2 Drawing Sheets

U.S. PATENT DOCUMENTS

| | | | | |
|---|---|---|---|---|
| 4,374,293 A * | 2/1983 | Burrington et al. | ........... | 585/410 |
| 4,853,357 A * | 8/1989 | Vasilevskis et al. | ......... | 502/165 |
| 5,324,702 A | 6/1994 | Yoo et al. | | |
| 5,330,955 A * | 7/1994 | Wegman | ..................... | 502/210 |
| 5,885,922 A * | 3/1999 | Hibst et al. | ................. | 502/305 |
| 5,985,788 A * | 11/1999 | Kishimoto et al. | .......... | 502/311 |
| 6,114,278 A * | 9/2000 | Karim et al. | ................ | 502/312 |
| 6,162,350 A * | 12/2000 | Soled et al. | ................. | 208/113 |
| 6,239,325 B1 * | 5/2001 | Kishimoto et al. | .......... | 585/658 |
| 6,274,765 B1 * | 8/2001 | Borchert et al. | ............. | 562/549 |
| 6,429,332 B1 * | 8/2002 | Tanimoto et al. | ............ | 562/532 |
| 6,458,737 B1 * | 10/2002 | Kishimoto et al. | .......... | 502/113 |
| 6,683,221 B1 * | 1/2004 | Wachs | ....................... | 568/475 |
| 7,129,195 B2 * | 10/2006 | Felder et al. | ................ | 502/311 |
| 7,288,182 B1 * | 10/2007 | Soled et al. | ................ | 208/112 |
| 2006/0094906 A1 | 5/2006 | Lee et al. | | |
| 2006/0281632 A1 * | 12/2006 | Lee et al. | .................... | 502/305 |

FOREIGN PATENT DOCUMENTS

| | | |
|---|---|---|
| JP | 48-47830 | 7/1973 |
| JP | 2001-198464 | 7/2001 |
| KR | 10-2006-0040147 | 5/2006 |

* cited by examiner

CATALYST FOR PARTIAL OXIDATION OF METHYLBENZENES, METHOD FOR PREPARING THE SAME, AND METHOD FOR PRODUCING AROMATIC ALDEHYDES USING THE SAME

This application claims priority to Korean Application 10-2006-0067396 filed on Jul. 19, 2006, which is incorporated by reference, as if fully set forth herein.

TECHNICAL FIELD

The present invention relates to a novel catalyst for gas phase oxidation of methylbenzenes in the presence of molecular oxygen to produce corresponding aromatic aldehydes, a method for preparing the catalyst, and a method for producing aromatic aldehydes from methylbenzenes by using the catalyst.

BACKGROUND ART

Aromatic aldehydes have a wide range of usage since they have aldehyde groups having high reactivity. Especially, terephthalaldehyde having two aldehyde groups at para position has been brought to attention as raw material for medicinal products, agrochemicals, pigments, liquid crystal polymers, or plastic having heat resistance.

Dehydration method of intermediate prepared by chlorination of p-xylene, and hydrogenation method of dimethyl terephthalate are conventional methods for the preparation of terephthalaldehyde known to the art. However, these conventional methods are not suitable for economical mass production since the processes are complicated and should be carried out under high pressure and non-environment-friendly conditions.

In order to solve these problems, there has been a continuous study for mass production of terephthalaldehyde by gas-phase-oxidizing p-xylene with molecular oxygen.

For example, Japanese Patent Publication No. 47-002086 discloses a complex oxide catalyst having the ratio range of W:Mo of from 1:1 to 20:1. And, Japanese Patent Publication No. 48-047830 discloses a catalyst comprising V and Rb or Cs. U.S. Pat. No. 3,845,137 discloses a catalyst consisting of two components, W and Mo, and one or more components selected from the group consisting of Ca, Ba, Ti, Zr, Hf, Tl, Nb, Zn, and Sn. Also, U.S. Pat. No. 4,017,547 discloses a catalyst consisting of Mo oxide, W oxide or silicotungstic acid and Bi oxide. However, the industrial practical use of these catalysts has been limited due to the low selectivity and yield of terephthalaldehyde.

Also, U.S. Pat. No. 5,324,702 discloses a catalyst comprising a first component selected from the group consisting of Fe, Zn, Zr, Nb, In, Sn, Sb, Ce and Bi, and a second component selected from the group consisting of V, Mo and W, wherein the first and second components are distributed on a deboronized borosilicate crystal molecular sieve by chemical vapor deposition (CVD). This catalyst shows relatively higher conversion rate to p-xylene, and relatively higher yield of terephthalaldehyde, than conventional catalysts. However, the catalyst has a limit in increasing the selectivity for various by-products, and so it was difficult to separate and purify it.

Also, Japanese Laid-open Patent Publication No. 2001-198464 discloses a catalyst comprising W as main component; one or more essential components selected from the group consisting of P, Sb, Bi and Si; and one or more optional components selected from the group consisting of Fe, Co, Ni, Mn, Re, Cr, V, Nb, Ti, Zr, Zn, Cd, Y, La, Ce, B, Al, Tl, Sn, Mg, Ca, Sr, Ba, Li, Na, K, Rb and Cs. The catalyst can provide high yield of terephthalaldehyde almost to the extent having industrial applicability. However, the catalyst also has limits in the separation and purification since the selectivity of terephthalaldehyde is not high, compared with the high conversion rate of p-xylene. Also, the catalyst has the problems of heat stability and life span since it comprises Sb component which is sublimated and lost at high temperature.

In short, in case of using the conventional catalysts, the terephthalaldehyde's yield is low. Or, the selectivity is low even though the yield is high. Thus, the separation and purification are difficult. Also, it is difficult to prepare the catalysts to have homogeneous composition and performance since they use a complex oxide having multiple components. Further, the catalysts comprise components having low heat stability, and so have short life span, and thus their industrial practical uses are limited.

On the other hand, Korean Patent Application No. 10-2004-0089376 filed by the present inventor disclosed a single-component catalyst comprising tungsten oxide, and fire-resistant inorganic carrier as optional component. The catalyst has advantages that it can be easily homogenous and has higher selectivity and yield of terephthalaldehyde than conventional complex oxide having multiple components. However, a catalyst having higher selectivity for preparing terephthalaldehyde has been still required because the future research trend of partial oxidation reaction process field will lie in development of a catalyst which can reduce the green house gas which is a major by-product, and can increase the selectivity of terephthalaldehyde, which will be very important standards for commercialization of catalyst process in the future.

DISCLOSURE OF THE INVENTION

The present invention intends to resolve the above problems. Thus, one object of the present invention is to provide a novel catalyst for gas phase oxidation of methylbenzenes which is suitable for producing corresponding aromatic aldehydes from methylbenzenes in high selectivity and high yield, and has homogenous composition and performance.

Another object of the present invention is to provide a method for preparing the catalyst according to the present invention.

Still, another object of the present invention is to provide a method for producing aromatic aldehydes from methylbenzenes by using the catalyst of the present invention in high selectivity and high yield.

The present invention relates to a catalyst for partial oxidation of methylbenzenes comprising the compound represented by the following formula (1) as active component:

$$W_a X_b Y_c O_x \qquad (1)$$

wherein W represents a tungsten atom,

X represents one or more alkali metals selected from the group consisting of Li, Na, K, Rb, and Cs, preferably one or more alkali metals selected from the group consisting of Na, K, Rb, and Cs Y represents one or more elements selected from the group consisting of Fe, Co, Ni, Cu, Mn, Re, Cr, V, Nb, Ti, Zr, Zn, Cd, Y, La, Ce, B, Al, Sn, Mg, Ca, Sr, and Ba, preferably one or more elements selected from the group consisting of Fe, Ce, Ni, Co, Sr, La, Cu, Zn and Zr, O stands for an oxygen atom, a, b, c and x each represent the atomic number of W, X, Y and O, respectively, the ratio of a:b:c is 12:0.001~1:0~5, preferably 12:0.005~1:0~2, more preferably 12:0.01~0.5:0~1, and x is a value determined by the oxidation state of W, X, and Y In the above, if b that is the ratio of component X is less than 0.001, the selectivity of the final product may be decreased, and if b is more than 1, the conversion rate may be rapidly decreased. Also, if c that is the ratio of component Y is more than 0.001, the selectivity of the final product may be decreased.

The present invention is characterized in adding a very small amount of alkali metal component into tungsten oxide to increase the selectivity and yield of the aromatic aldehyde and to improve the heat stability of the catalyst. The catalyst for partial oxidation represented by the above formula (1) comprises a binary system comprising tungsten and one kind of alkali metal, for example, $W_{12}Rb_{0.02}$, $W_{12}R_{0.03}$, $W_{12}Cs_{0.02}$, $W_{12}Cs_{0.03}$, $W_{12}Na_{0.025}$, or $W_{12}K_{0.02}$; a tertiary system comprising tungsten, an alkali metal and a third component, for example, $W_{12}Rb_{0.02}Fe_{0.05}$, $W_{12}Rb_{0.02}Fe_{0.2}$, $W_{12}Rb_{0.2}Fe_{0.5}$, $W_{12}Rb_{0.02}Ce_{0.3}$, $W_{12}Rb_{0.02}Ni_{0.1}$, $W_{12}R_{0.02}Co_{0.1}$, $W_{12}R_{0.02}Sr_{0.01}$, $W_{12}R_{0.02}La_{0.3}$, $W_{12}Rb_{0.02}Cu_{0.1}$, $W_{12}Rb_{0.02}Zn_{0.1}$, or $W_{12}Rb_{0.02}Zr_{0.1}$; and a tertiary system comprising tungsten and two kinds of alkali metals, for example, $W_{12}Rb_{0.01}K_{0.01}$, $W_{12}Rb_{0.01}Cs_{0.01}$, or $W_{12}Rb_{0.015}Cs_{0.005}$.

The catalyst for partial oxidation of the present invention can be supported on a fire-resistant inorganic support in order to improve the activity, selectivity or physical durability. Typical examples of such fire-resistant inorganic support are alumina such as α-alumina, silica, titania, zirconia, silicon carbide, etc.

In case the active component of the above formula is supported on a fire-resistant inorganic support, the supporting amount is at least 5 wt %, preferably at least 12 wt %, and more preferably at least 15~90 wt %, of the sum of the support weight plus the catalytic active component weight, in view of the objects of the present invention. If the amount is below 5 wt %, the required reaction activity and selectivity of terephthalaldehyde cannot be attained.

The supporting amount may depend on the pore volume of the support, and the support with larger pore volume is advantageous in that the supporting amount can be increased.

Also, according to the present inventors' experiments, the conversion rate is improved, but the selectivity is decreased, as the surface area of the support is increased. From their several experiments, it was shown that a support having the surface area of 0.5 $m^2/g$ or less, preferably 0.1 $m^2/g$ or less, and more preferably in the range of 0.005 $m^2/g$ to 0.05 $m^2/g$, is advantageous in view of the conversion rate of methylbenzenes and the selectivity of terephthalaldehyde since the complete oxidation of methylbenzenes and side reactions can be prevented. Within the above range, the conversion rate increases, as the surface area increases.

Further, a support having an average pore size of at least 10 μm, preferably at least 50 μm, is advantageous in obtaining the desired selectivity of terephthalaldehyde.

The shape of inorganic carrier or catalyst prepared thereby is not particularly limited, and spheres, pellets, rings, honeycomb, etc. can be selectively used. Further, not only molded products but also oxide or hydroxide powders, gels, sols, etc. can be selectively used.

The present invention also relates to a method for preparing the catalyst of the formula (1), $$WaXbYcOx \quad (1)$$

wherein W represents a tungsten atom,

X represents one or more alkali metals selected from the group consisting of Li, Na, K, Rb, and Cs, Y represents one or more elements selected from the group consisting of Fe, Co, Ni, Cu, Mn, Re, Cr, V, Nb, Ti, Zr, Zn, Cd, Y, La, Ce, B, Al, Sn, Mg, Ca, Sr and Ba, O stands for an oxygen atom, a, b, c and x each represent the atomic number of W, X, Y and O, respectively, the ratio of a:b:c is 12:0.001~1:0~5, and x is a number determined by the oxidation state of W, X, and Y, for partial oxidation of methylbenzenes, the method comprising:

(a) a step of preparing a solution or slurry of the compounds comprising raw material of tungsten and raw material of alkali metal selected from the group consisting of Li, Na, K, Rb, and Cs;

(b) a step of drying said solution or slurry; and (c) a step of calcining the product obtained in the step (b).

Only, the above preparation method is one embodiment of the process for preparing the catalyst for partial oxidation of the present invention, and the catalyst of the present invention may be prepared by any conventional catalyst preparation method.

Hereinafter, each step of the present invention will be described more specifically.

The step (a) of the present invention is a step of preparing a solution or slurry of the compounds comprising raw material of tungsten and raw material of alkali metal selected from the group consisting of Li, Na, K, Rb, and Cs.

The above compounds comprising raw material of tungsten are not specially limited, but oxides, carbides, chlorides, sulfides, silicides, organic acid salt, or heteropolyacid in addition to ammonium tungstate may be used. It is more preferable to use a tungsten oxide prepared by calcining ammonium metatungstate hydrate. Also, the raw materials of alkali metal are not specially limited, but nitrates, hydroxides, carbides, or oxides may be used. The solution or slurry may optionally comprise a raw material of Y, i.e., one or more elements selected from the group consisting of Fe, Co, Ni, Cu, Mn, Re, Cr, V, Nb, Ti, Zr, Zn, Cd, Y, La, Ce, B, Al, Sn, Mg, Ca, Sr, and Ba. The raw materials of Y also are not specially limited, but nitrates, hydroxides, carbides, or oxides may be used.

Also, it is preferable to prepare the catalyst as solution rather than slurry in view of the catalyst's homogeneity. The solvents used for preparing the solution or slurry of the compounds comprising tungsten also are not specially limited. As the solvent, water, or alcohols including methanol, ethanol, propanol, and diols may be used. It is preferable to use water in the environmental aspect. The water includes distilled water and de-mineralized water.

The preferable method for preparing the catalyst of the formula (1) for partial oxidation of methylbenzenes further comprises the step (d) of supporting the solution or slurry obtained in the step (a) on inorganic carrier.

In the above step (d) of the present invention, the suitable ratio of the pore volume of inorganic carrier and the volume of the solution or slurry in the step (b) is 1:0.9~1.1, preferably, 1:0.95~1.05. It is most preferable to support the corresponding volume of solution or slurry to the pore volume of carrier in view of the yield or selectivity.

For the above inorganic carrier, it is preferable to use one or more fire-resistant inorganic carriers selected from the group consisting of α-alumina, silica, titania, zirconia and silicon carbide.

Also, the step (d) is preferable to be carried out under reduced pressure or vacuum condition since the reduced pressure or vacuum of a container having carrier can support the active ingredient on the inner surface of the catalyst.

The steps (b) and (c) of the present invention are the steps of drying and calcining the prepared catalyst.

When the catalyst is dried or calcined in the present invention, the method or atmosphere is not particularly limited. For example, the method may include vacuum dry, refrigeration dry, spray dry, microwave dry, rotary evaporation, air dry, etc. The atmosphere may be air, oxygen-rich or oxygen-lean atmosphere, reducing atmosphere, inert gas atmosphere, or vacuum.

The temperature conditions of the above steps (b) and (c) also are not particularly limited, but the preferable dry temperature is 80~200° C., and the preferable calcination temperature is 300~700° C. When the dry temperature is less than 80° C., the dry efficiency may be decreased. When the dry temperature is more than 200° C., the catalyst performance may be decreased. When the calcination temperature is less than 300° C., it is difficult to remove the reaction impurities, and when the temperature is more than 700° C., the morphology of the catalyst may be deformed. The time conditions of the above steps (b) and (c) are not particularly limited, but each step of (b) and (c) is preferable to be carried out for a sufficient time of more than 2 hours.

Further, according to the present method, it is preferable that the above supporting and drying steps [steps (d) and (b)] are repeatedly carried out at least two times. The frequency of repeating the supporting and drying steps is not particularly limited, but more repetitions are advantageous since more repetitions lead to increase of the amount of supported material, which leads again to increase of the conversion rate. That is, the steps (d) and (b) are preferable to be repeated at least two times, more preferably at least three times, since the concentration of raw material in aqueous solution or slurry is limited. Specifically, the steps (d) and (b) are preferable to be repeated until 80% or more of pore volume of inorganic carrier is supported as the active compounds. In this case, the frequency of repetition of the above steps depends on the concentration of the active compounds in aqueous solution or slurry.

Also, the present invention relates to a method for producing aromatic aldehydes corresponding to methylbenzenes that are oxidized in gas phase with using molecular oxygen by using the catalyst according to the present invention.

The term "methylbenzene" used herein means any compound having one or more methyl groups directly joined to the benzene ring, and may include methylbenzenes containing 7 to 10 carbon atoms, such as p-xylene, o-xylene, m-xylene, psudocumene, mesitylene, and durene, but is not limited thereto.

The present method for producing aromatic aldehydes may comprises preparing terephthalaldehyde and p-tolualdehyde from p-xylene; phthalaldehyde and o-tolualdehyde from o-xylene; isophtalaldehyde and m-tolualdehyde from m-xylene; 2-methylterephthalaldehyde, 2,4-dimethylbenzaldehyde, 2,5-dimethylbenzaldehyde, and 3,4-dimethylbenzaldehyde from pseudocumene; 3,5-dimethylbenzaldehyde, 5-methylisophthalaldehyde and 1,3,5-triformylbenzene from mesitylene; and 2,5-dimethylterephthalaldehyde, 4,5-dimethylphthalaldehyde, 2,4,5-trimethylbenzaldehyde, 2,4,5-triformyltoluene and 1,2,4,5-tetraformylbenzene from durene; but is not limited thereto. Particularly, the catalyst for partial oxidation of methylbenzenes prepared by the present invention is suitable for preparing terephthalaldehyde from p-xylene.

Besides methylbenzene and molecular oxygen as raw materials, diluent gas may be used, if necessary. And, air or pure oxygen may be used as source of the molecular oxygen. In general, the molecular oxygen is used in 3~100 moles per mole of methylbenzene. For the diluent gas, inert gas such as nitrogen, helium, argon, etc.; carbon dioxidel; or water vapor can be used.

The reaction conditions of oxidation of methylbenzene in gas phase in the present invention are not particularly limited. The reaction may be performed by contacting the source gas with the catalyst at a space velocity of 1,000~100,000 hr$^{-1}$, preferably 1,000~50,000 hr$^{-1}$, and a reaction temperature of 350-700° C., preferably 450-650° C. Also, the reaction is generally performed at normal pressure or slightly elevated pressure, but can be performed at high or reduced pressure. Moreover, the reaction system is not particularly limited, and may be one-pass system or recycling system. Further, the reaction can be performed on fixed bed, mobile bed, fluidized bed, etc.

BEST MODE FOR CARRYING OUT THE INVENTION

Figure 1:
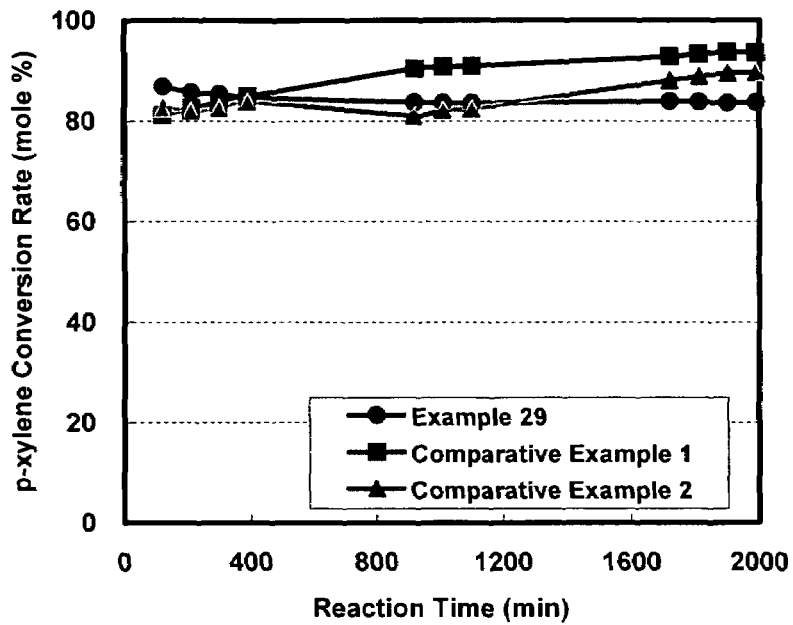
FIG. 1 is a graph representing p-xylene conversion rate depending on reaction time of catalyst according to an example of the present invention.

Hereinafter, the present invention will be more specifically illustrated by the following examples. However, the following examples should not be construed as limiting the scope of the present invention in any way.

The conversion rate, selectivity, and one-pass yield of the reaction are defined taking by-products into account as follows:

Conversion rate (mole %)=(the number of moles of reacted starting compound/the number of moles of fed starting compound)×100

Selectivity (mole %)=(the number of moles of each product compound/the number of moles of reacted starting compound)×(the number of carbon atoms of each product compound/the number of carbon atoms of fed starting compound)×100

One-pass yield (mole %)=(the number of moles of each product compound/the number of moles of fed starting compound)×(the number of carbon atoms of each product compound/the number of carbon atoms of fed starting compound)×100

EXAMPLE 1

Ammonium metatungstate hydrate ((NH4)$_6$.W$_{12}$O$_{39}$.xH$_2$O)) was used as a precursor of tungsten oxide. The ammonium metatungstate hydrate was calcinated at 650° C. for 2 hours under the air atmosphere to obtain tungsten oxide. And, a rubidium nitrate solution having 0.1 mmol/g of rubidium concentration was prepared by dissolving rubidium nitrate (RbNO$_3$) of 1.47 g in water of 98.53 g. The diluted solution having the total weight of 10 g was prepared by adding water into the rubidium nitrate solution of 0.4 g, and tungsten oxide powder of 5.564 g was added thereto, followed by heating and agitation in water bath to carry out evaporation. Thus obtained product was dried in an oven of 120° C. for 18 hours, followed by calcining in the furnace of 650° C. for 2 hours under the air atmosphere. The catalyst composition prepared by the above process is $W_{12}Rb_{0.02}$.

Thus obtained catalyst powder was pressurized to prepare pellet, and thus obtained pellet was pulverized and meshed to select catalyst particles having the size of 200 μm. The evaluation experiment was carried out by using the selected catalyst.

A continuous flow reactor with quartz was used for the above experiment. The catalyst of 0.2 g was filled in the quartz reactor, and gas phase oxidation reaction was performed under the following conditions by passing p-xylene and air as reactants:

Reaction pressure: normal pressure
The ratio of gas reactant (volume ratio):
p-xylene/oxygen/nitrogen=0.5/12.5/87(oxygen/p-xylene=25)
Total feeding rate of gas reactant: 100 cc/min
Reaction temperature: 520, 550, and 580° C.

The test results of the experiment were shown in the following Tables 1 and 2 and FIGS. 1 to 3.

The following examples and comparative examples were carried out by using the catalyst having the particle size of 200 μm prepared by the same method as Example 1 under the same conditions as the above, unless mentioned otherwise.

EXAMPLE 2

The catalyst having the composition of $W_{12}Rb_{0.03}$ was prepared by the same manner as Example 1 except using rubidium nitrate solution of 0.6 g.

EXAMPLE 3

A cesium nitrate ($CsNO_3$) solution was prepared with cesium as raw material. The cesium nitrate solution having 0.1 mmol/g of cesium concentration was prepared by dissolving cesium nitrate of 1.95 g in water of 98.05 g. The diluted solution having the total weight of 10 g was prepared by adding water into the cesium nitrate solution of 0.4 g. The catalyst having the composition of $W_{12}Cs_{0.02}$ was prepared in the same manner as Example 1 except the above.

EXAMPLE 4

The catalyst having the composition of $W_{12}Cs_{0.03}$ was prepared in the same manner as Example 1 except using cesium nitrate solution of 0.6 g.

EXAMPLE 5

A sodium nitrate ($NaNO_3$) solution was prepared with cesium as raw material. The sodium nitrate solution having 0.1 mmol/g of sodium concentration was prepared by dissolving sodium nitrate of 0.85 g in water of 99.15 g. The diluted solution having the total weight of 10 g was prepared by adding water into the sodium nitrate solution of 0.5 g. The catalyst having the composition of $W_{12}Na_{0.025}$ was prepared in the same manner as Example 1 except the above.

EXAMPLE 6

A potassium nitrate ($KNO_3$) solution was prepared with potassium as raw material. The potassium nitrate solution having 0.1 mmol/g of potassium concentration was prepared by dissolving potassium nitrate of 1.01 g in water of 98.99 g. The diluted solution having the total weight of 10 g was prepared by adding water into the potassium nitrate solution of 0.4 g. The catalyst having the composition of $W_{12}K_{0.02}$ was prepared in the same manner as Example 1 except the above.

EXAMPLES 7 TO 10

The reaction was carried out by using the same catalyst in the same manner as Example 1, except that the catalyst amounts filled in the reactor was changed to 0.6, 0.8, 1.0, and 1.5 g, respectively.

EXAMPLES 11 TO 13

The reaction was carried out by using the same catalyst as Example 3 in the same manner as Example 1, except that the catalyst amounts filled in the reactor was changed to 0.6, 0.8, 1.0, and 1.2 g, respectively.

EXAMPLE 14

An iron nitrate (III) nonahydrate ($FeN_3O_9.9H_2O$) solution was prepared with iron as raw material. The iron nitrate solution having 0.1 mmol/g of iron concentration was prepared by dissolving iron nitrate of 4.04 g in water of 95.96 g. The solution having the total weight of 10 g was prepared by mixing the iron nitrate solution of 1.0 g and the rubidium nitrate solution of 0.4 g of Example 1, and adding water thereto. The catalyst having the composition of $W_{12}Rb_{0.02}Fe_{0.05}$ was prepared in the same manner as Example 1 except the above.

EXAMPLE 15

The catalyst having the composition of $W_{12}Rb_{0.02}Fe_{0.2}$ was prepared in the same manner as Example 14, except using the iron nitrate solution of 4.0 g.

EXAMPLE 16

The catalyst having the composition of $W_{12}Rb_{0.2}Fe_{0.5}$ was prepared in the same manner as Example 14, except using the iron nitrate solution of 10 g and the rubidium nitrate solution of 4 g.

EXAMPLE 17

The reaction was carried out by using the same catalyst as in Example 14 in the same manner as Example 1, except that the catalyst amount filled in the reactor was changed to 0.3 g.

EXAMPLE 18

A cerium (III) nitrate ($CeN_3O_9.6H_2O$) solution was prepared with cerium as raw material. The cerium nitrate solution having 0.1 mmol/g of cerium concentration was prepared by dissolving cerium nitrate of 4.34 g in water of 95.65 g. The catalyst having the composition of $W_{12}Rb_{0.02}Ce_{0.3}$ was prepared in the same manner as Example 14, except using the cerium nitrate solution of 6.0 g. The reaction was carried out in the same manner as Example 1, except that the catalyst amount filled in the reactor was changed to 0.6 g.

EXAMPLE 19

A nickel (II) nitrate ($NiN_2O_6.6H_2O$) solution was prepared with nickel as raw material. The nickel nitrate solution having 0.1 mmol/g of nickel concentration was prepared by dissolving nickel nitrate of 2.91 g in water of 97.09 g. The catalyst having the composition of $W_{12}Rb_{0.02}Ni_{0.1}$ was prepared in the same manner as Example 14, except using the nickel nitrate solution of 2.0 g. The reaction was carried out in the same manner as Example 1, except that the catalyst amount filled in the reactor was changed to 1.2 g.

EXAMPLE 20

A cobalt (II) nitrate ($CoN_2O_6.6H_2O$) solution was prepared with cobalt as raw material. The cobalt nitrate solution having 0.1 mmol/g of cobalt concentration was prepared by dissolving cobalt nitrate of 2.91 g in water of 97.09 g. The catalyst having the composition of $W_{12}Rb_{0.02}Co_{0.1}$ was prepared in the same manner as Example 14, except using the cobalt nitrate solution of 2.0 g. The reaction was carried out in the same manner as Example 1, except that the catalyst amount filled in the reactor was changed to 1.2 g.

EXAMPLE 21

A strontium (II) nitrate ($SrN_2O_6$) solution was prepared with strontium as raw material. The strontium nitrate solution having 0.1 mmol/g of strontium concentration was prepared by dissolving strontium nitrate of 2.12 g in water of 97.88 g. The catalyst having the composition of $W_{12}Rb_{0.02}Sr_{0.1}$ was prepared in the same manner as Example 14, except using the strontium nitrate solution of 2.0 g. The reaction was carried out in the same manner as Example 1, except that the catalyst amount filled in the reactor was changed to 1.2 g.

EXAMPLE 22

A lanthanum (III) nitrate ($LaN_3O_9.6H_2O$) solution was prepared with lanthanum as raw material. The lanthanum nitrate solution having 0.1 mmol/g of lanthanum concentration was prepared by dissolving lanthanum nitrate of 4.33 g in water of 95.67 g. The catalyst having the composition of $W_{12}Rb_{0.02}La_{0.3}$ was prepared in the same manner as Example 14, except using the lanthanum nitrate solution of 6.0 g. The reaction was carried out in the same manner as Example 1, except that the catalyst amount filled in the reactor was changed to 1.2 g.

EXAMPLE 23

A copper (II) nitrate ($CuN_2O_6.3H_2O$) solution was prepared with copper as raw material. The copper nitrate solution having 0.1 mmol/g of copper concentration was prepared by dissolving copper nitrate of 2.42 g in water of 97.58 g. The catalyst having the composition of $W_{12}Rb_{0.02}Cu_{0.1}$ was prepared in the same manner as Example 14, except using the copper nitrate solution of 2.0 g. The reaction was carried out in the same manner as Example 1, except that the catalyst amount filled in the reactor was changed to 0.8 g.

EXAMPLE 24

A zinc nitrate ($ZnN_2O_6.6H_2O$) solution was prepared with zinc as raw material. The zinc nitrate solution having 0.1 mmol/g of zinc concentration was prepared by dissolving zinc nitrate of 2.97 g in water of 97.03 g. The catalyst having the composition of $W_{12}Rb_{0.02}Zn_{0.1}$ was prepared in the same manner as Example 14, except using the zinc nitrate solution of 2.0 g. The reaction was carried out in the same manner as Example 1, except that the catalyst amount filled in the reactor was changed to 1.2 g.

EXAMPLE 25

A zirconyl (IV) nitrate hydrate ($ZrN_2O_7.xH_2O$) solution was prepared with zirconium as raw material. The zirconium nitrate solution having 0.1 mmol/g of zirconium concentration was prepared by dissolving zirconium nitrate of 2.31 g in water of 97.69 g. The catalyst having the composition of $W_{12}Rb_{0.02}Zr_{0.1}$ was prepared in the same manner as Example 14, except using the zirconium nitrate solution of 2.0 g. The reaction was carried out in the same manner as Example 1, except that the catalyst amount filled in the reactor was changed to 1.2 g.

EXAMPLE 26

The homogeneous precipitation solution having the total weight of 10 g was prepared by mixing the rubidium nitrate solution of 0.2 g of Example 1 and the potassium nitrate solution of 0.2 g of Example 3, and adding water thereto. The catalyst having the composition of $W_{12}Rb_{0.01}K_{0.01}$ was prepared in the same manner as Example 1 except the above. The reaction was carried out in the same manner as Example 1, except that the catalyst amount filled in the reactor was changed to 1.2 g.

EXAMPLE 27

The homogeneous precipitation solution having the total weight of 10 g was prepared by mixing the rubidium nitrate solution of 0.2 g of Example 1 and the cesium nitrate solution of 0.2 g, and adding water thereto. The catalyst having the composition of $W_{12}Rb_{0.01}Cs_{0.01}$ was prepared in the same manner as Example 1, except the above. The reaction was carried out in the same manner as Example 1, except that the catalyst amount filled in the reactor was changed to 1.2 g.

EXAMPLE 28

The catalyst having the composition of $W_{12}Rb_{0.015}Cs_{0.005}$ was prepared in the same manner as Example 27 except using the rubidium nitrate solution of 0.3 g and the cesium nitrate solution of 0.1 g. The reaction was carried out in the same manner as Example 1 except that the catalyst amount filled in the reactor was changed to 1.2 g.

EXAMPLE 29

The reaction was carried out by using the same catalyst as in Example 1. The catalyst of 1.2 g was filled in the reactor, and the reaction was carried out at the temperature of 550° C. for 400 min. Then, the reaction was continued at the temperature of 580° C. for 400 min, 550° C. for 400 min, 600° C. for 400 min, and 550° C. for 400 min, in sequence. The reaction was carried out under the same conditions as Example 1, except changing the filled amount of catalyst and temperature.

COMPARATIVE EXAMPLE 1

An ammonium metatungstate solution of 2 mmol/g was prepared by dissolving ammonium metatungstate hydrate of 49.27 g as raw material of tungsten in water of 50.73 g. Also, a tartaric acid-antimony solution was prepared with antimony as raw material. The tartaric acid-antimony solution having 0.5 mmol/g of antimony concentration was prepared by adding L-tartaric acid of 60 g and antimony(III) oxide ($Sb_2O_3$) of 14.7 g into water of 125.3 g, followed by heating and reflux.

Further, an iron nitrate (III) nonahydrate (FeN$_3$O$_9$.9H$_2$O) solution was prepared with iron as raw material. The iron nitrate solution having 1 mmol/g of iron concentration was prepared by dissolving iron nitrate of 40.4 g in water of 59.6 g. The iron nitrate solution of 2 g was added into the tartaric acid-antimony solution of 6 g, and the ammonium metatungstate solution of 6 g was added thereto to obtain a homogeneous precipitation solution. The obtained solution was heated and agitated in water bath to carry out evaporation. Thus obtained product was dried in an oven of 120° C. for 18 hours, followed by calcining in the furnace of 650° C. for 2 hours under the air atmosphere. The catalyst composition prepared by the above process is W$_{12}$Sb$_3$Fe$_2$.

This catalyst of 0.1 g was filled in the reactor, and the reaction was performed under the same temperature condition as Example 29.

COMPARATIVE EXAMPLE 2

A solution having the total weight of 10 g was prepared by adding water into the tartaric acid solution (0.5 mmol/g) of Comparative Example 1. The tungsten oxide powder (5.564 g) prepared by the same method as Example 1 was added thereto, followed by heating and agitation in water bath to carry out evaporation. Thus obtained product was dried in an oven of 120° C. for 18 hours, followed by calcining in the fuimace of 650° C. for 2 hours under the air atmosphere. The catalyst composition prepared by the above process is W$_{12}$Sb$_1$.

This catalyst of 0.5 g was filled in the reactor, and the reaction was performed under the same temperature condition as Example 29.

TABLE 1

| | Amount of catalyst (g) | Temp. (° C.) | p-Xylene Con. Rate (mol %) | TPAL Selectivity (mol %) | TPAL Yield (mol %) |
|---|---|---|---|---|---|
| Ex. 1 | 0.2 | 550 | 27.2 | 83.2 | 22.7 |
| Ex. 2 | 0.2 | 550 | 20.6 | 80.0 | 16.5 |
| Ex. 3 | 0.2 | 550 | 30.9 | 78.5 | 24.3 |
| Ex. 4 | 0.2 | 550 | 21.1 | 79.1 | 16.7 |
| Ex. 5 | 0.2 | 580 | 64.3 | 69.3 | 44.6 |
| Ex. 6 | 0.2 | 550 | 29.0 | 76.4 | 22.2 |
| Ex. 7 | 0.6 | 550 | 58.9 | 85.0 | 50.0 |
| Ex. 8 | 0.8 | 550 | 71.6 | 81.8 | 58.6 |
| Ex. 9 | 1.0 | 550 | 76.0 | 80.5 | 61.2 |
| Ex. 10 | 1.5 | 550 | 86.8 | 74.0 | 64.3 |
| Ex. 11 | 0.6 | 550 | 62.6 | 82.8 | 51.8 |

TABLE 1-continued

| | Amount of catalyst (g) | Temp. (° C.) | p-Xylene Con. Rate (mol %) | TPAL Selectivity (mol %) | TPAL Yield (mol %) |
|---|---|---|---|---|---|
| Ex. 12 | 1.0 | 550 | 76.6 | 80.6 | 61.7 |
| Ex. 13 | 1.2 | 550 | 81.4 | 77.1 | 62.8 |
| Ex. 14 | 0.2 | 550 | 71.7 | 75.4 | 54.0 |
| Ex. 15 | 0.2 | 550 | 76.8 | 73.8 | 56.7 |
| Ex. 16 | 0.2 | 550 | 53.6 | 71.0 | 38.1 |
| Ex. 17 | 0.3 | 550 | 82.3 | 73.5 | 60.5 |
| Ex. 18 | 0.6 | 550 | 80.2 | 75.5 | 60.5 |
| Ex. 19 | 1.2 | 550 | 84.8 | 72.9 | 61.8 |
| Ex. 20 | 1.2 | 550 | 81.0 | 76.5 | 61.9 |
| Ex. 21 | 1.2 | 550 | 65.4 | 82.4 | 53.9 |
| Ex. 22 | 1.2 | 550 | 67.3 | 60.2 | 40.5 |
| Ex. 23 | 0.8 | 520 | 68.0 | 66.9 | 45.4 |
| Ex. 24 | 1.2 | 550 | 75.4 | 72.4 | 54.6 |
| Ex. 25 | 1.2 | 550 | 90.8 | 66.1 | 60.0 |
| Ex. 26 | 1.2 | 520 | 84.8 | 73.4 | 62.3 |
| Ex. 27 | 1.2 | 550 | 73.0 | 74.5 | 54.4 |
| Ex. 28 | 1.2 | 520 | 67.7 | 75.2 | 50.9 |

TPAL: terephthalaldehyde

TABLE 2

| | Example 29 | | | Comparative Example 1 | | | Comparative Example 2 | | |
|---|---|---|---|---|---|---|---|---|---|
| Time (min) | p-Xylene Con. Rate (mol %) | TPAL Selectivity (mol %) | TPAL Yield (mol %) | p-Xylene Con. Rate (mol %) | TPAL Selectivity (mol %) | TPAL Yield (mol %) | p-Xylene Con. Rate (mol %) | TPAL Selectivity (mol %) | TPAL Yield (mol %) |
| 120 | 86.7 | 74.4 | 64.5 | 81.2 | 68.6 | 55.7 | 82.4 | 58.5 | 48.2 |
| 210 | 85.6 | 74.4 | 63.7 | 82.5 | 67.9 | 56.0 | 82.0 | 56.8 | 46.6 |
| 300 | 85.3 | 74.7 | 63.7 | 83.6 | 67.0 | 56.0 | 82.6 | 56.8 | 46.9 |
| 390 | 84.7 | 74.6 | 63.2 | 84.8 | 67.1 | 56.9 | 83.9 | 57.3 | 48.1 |
| 920 | 83.7 | 74.5 | 62.3 | 90.3 | 61.5 | 55.5 | 81.0 | 53.4 | 43.3 |
| 1010 | 83.6 | 74.4 | 62.2 | 90.7 | 61.5 | 55.8 | 82.2 | 52.7 | 43.3 |
| 1100 | 83.6 | 74.1 | 61.9 | 90.8 | 60.4 | 54.9 | 82.5 | 52.3 | 43.1 |
| 1720 | 83.9 | 75.3 | 63.1 | 92.7 | 57.8 | 53.6 | 88.0 | 46.8 | 41.1 |
| 1810 | 83.8 | 75.3 | 63.0 | 93.2 | 58.3 | 54.3 | 88.8 | 46.3 | 41.1 |
| 1900 | 83.5 | 75.8 | 63.3 | 93.6 | 58.4 | 54.6 | 89.4 | 45.7 | 40.9 |
| 1990 | 83.6 | 75.7 | 63.3 | 93.5 | 58.3 | 54.5 | 89.5 | 45.3 | 40.5 |

INDUSTRIAL APPLICABILITY

According to the Examples 1 to 4 of the present invention, the catalyst comprising alkali metal showed high selectivity of terephthalaldehyde. Also, the Examples 7 to 13 showed that the catalyst comprising rubidium or cesium can increase the yield of terephthalaldehyde since the conversion rate of p-xylene is increased, and the selectivity of terephthalaldehyde is maintained as the filled amount of catalyst is increased.

Figure 2:
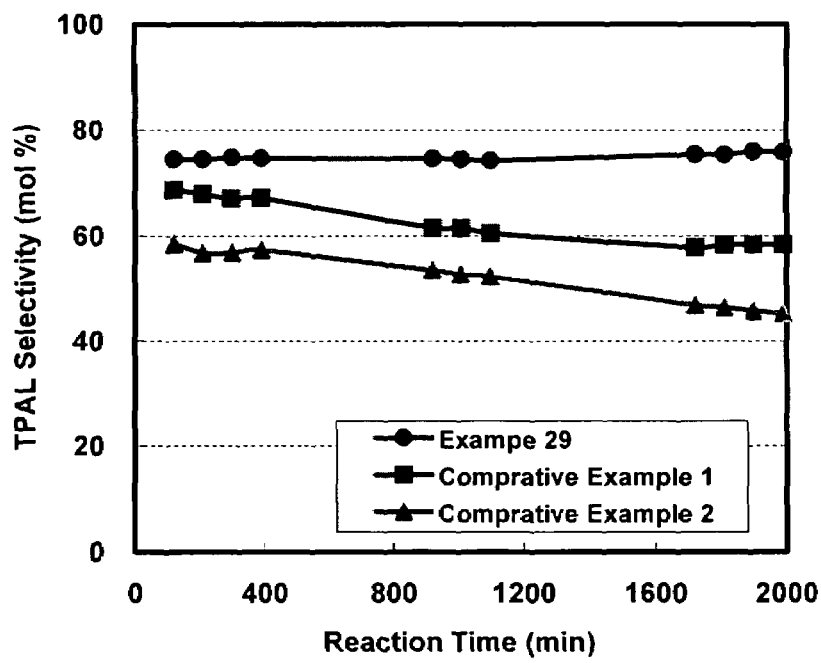
FIG. 2 is a graph representing terephthal aldehyde (TPAL) selectivity depending on reaction time of catalyst according to an example of the present invention.
Figure 3:
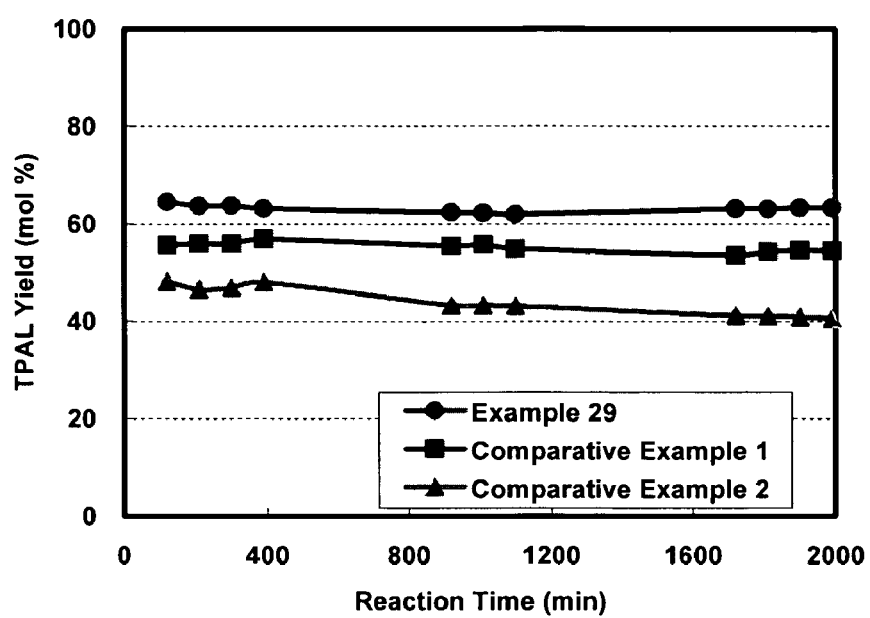
FIG. 3 is a graph representing terephthal aldehyde (TPAL) yield depending on reaction time of catalyst according to an example of the present invention.

Further, according to Table 2, and FIGS. 1 to 3, the catalyst of Example 29 can maintain the conversion rate of p-xylene and the selectivity of terephthalaldehyde constantly during the reaction time. However, in the catalyst of Comparative Examples 1 and 2, the selectivity is decreased as the yield of terephthalaldehyde is decreased, even though the conversion rate is increased.

What is claimed is:

1. A catalyst for partial oxidation of methylbenzenes comprising a compound represented by the following formula (1) as an active component:

$$WaXbYcOx \qquad (1)$$

wherein W represents a tungsten atom,
X represents one or more alkali metals selected from the group consisting of Li, Na, K, Rb, and Cs,
Y represents one or more elements selected from the group consisting of Fe, Co, Ni, Cu, Mn, Re, Cr, V, Nb, Ti, Zr, Zn, Cd, Y, La, Ce, B, Al, Sn, Mg, Ca, Sr, and Ba, O stands for an oxygen atom, a, b, c and x each represent the atomic number of W, X, Y and O, respectively, the ratio of a:b:c is 12:0.001~1:0~5, and x is a number determined by the oxidation state of W, X, and Y.

2. The catalyst according to claim 1, wherein X represents one or more alkali metals selected from the group consisting of Na, K, Rb, and Cs.

3. The catalyst according to claim 1, wherein Y represents one or more elements selected from the group consisting of Fe, Ce, Ni, Co, Sr, La, Cu, Zn and Zr.

4. The catalyst according to claim 1, wherein the ratio of a:b:c is 12:0.001~0.5:0~1.

5. The catalyst according to claim 1, wherein the compound represented by the formula (1) is supported on a fire-resistant inorganic support.

6. A method for producing aromatic aldehydes from partial oxidation of methylbenzenes in gas phase using molecular oxygen by using the catalyst according to any one of claims 1 to 5.

7. The method according to claim 6, wherein the methylbenzenes have 7 to 10 carbon atoms.

8. The method of according to claim 6, wherein the methylbenzenes are p-xylene, and the corresponding aromatic aldehyde produced thereby is terephthalaldehyde.

9. A method for preparing a catalyst of the formula (1), $$W_a X_b Y_c O_x \qquad (1)$$

wherein W represents a tungsten atom,

X represents one or more alkali metals selected from the group consisting of Li, Na, K, Rb, and Cs, Y represents one or more elements selected from the group consisting of Fe, Co, Ni, Cu, Mn, Re, Cr, V, Nb, Ti, Zr, Zn, Cd, Y, La, Ce, B, Al, Sn, Mg, Ca, Sr and Ba, O stands for an oxygen atom, a, b, c and x each represent the atomic number of W, X, Y and O, respectively, the ratio of a:b:c is 12:0.001~1:0~5, and x is a number determined by the oxidation states of W, X, and Y, for partial oxidation of methylbenzenes, the method comprising:

(a) a step of preparing a solution or slurry of compound comprising raw material of tungsten and raw material of alkali metal selected from the group consisting of Li, Na, K, Rb, and Cs;

(b) a step of drying said solution or slurry; and (c) a step of calcining a product obtained in the step (b).

10. The method according to claim 9, wherein the method further comprises a step of supporting the solution or slurry obtained in the step (a) on inorganic carrier.

11. The method according to claim 9, wherein the raw material of tungsten is tungsten oxide prepared by calcining ammonium metatungstate hydrate.

12. The method according to claim 9, wherein the step (b) is carried out at a temperature of 80~200° C.

13. The method according to claim 9, wherein the step (c) is carried out at a temperature of 300~700° C.

* * * * *